United States Patent
Quach et al.

(10) Patent No.: US 9,694,171 B2
(45) Date of Patent: *Jul. 4, 2017

(54) COLLAPSIBLE VALVE WITH INTERNAL DIMPLES

(71) Applicant: CareFusion 303, Inc., San Diego, CA (US)

(72) Inventors: Matthew Quach, San Gabriel, CA (US); Christopher J. Zollinger, Chino Hills, CA (US); Jonathan Yeh, Diamond Bar, CA (US); George Michel Mansour, Pomona, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/040,891

(22) Filed: Feb. 10, 2016

(65) Prior Publication Data

US 2016/0158524 A1 Jun. 9, 2016

Related U.S. Application Data

(63) Continuation of application No. 13/801,399, filed on Mar. 13, 2013, now Pat. No. 9,278,205.

(51) Int. Cl.
*A61M 39/22* (2006.01)
*A61M 39/24* (2006.01)
(Continued)

(52) U.S. Cl.
CPC ............ *A61M 39/22* (2013.01); *A61M 39/10* (2013.01); *A61M 39/24* (2013.01); *A61M 39/26* (2013.01); *A61M 2039/2433* (2013.01)

(58) Field of Classification Search
CPC ...... A61M 39/22; A61M 39/10; A61M 39/26; A61M 39/24; A61M 2039/2433
See application file for complete search history.

(56) References Cited

U.S. PATENT DOCUMENTS

| 4,141,379 A | 2/1979 | Manske |
| 4,535,820 A | 8/1985 | Raines |

(Continued)

FOREIGN PATENT DOCUMENTS

| CN | 1077654 A | 10/1993 |
| CN | 1139010 A | 1/1997 |

(Continued)

OTHER PUBLICATIONS

International Search Report and Written Opinion for the International Preliminary Examining Authority for Application No. PCT/US2014/017828, dated Mar. 20, 2015, 6 pages.

(Continued)

*Primary Examiner* — Theodore Stigell
*Assistant Examiner* — Amber Stiles
(74) *Attorney, Agent, or Firm* — McDermott Will & Emery LLP

(57) ABSTRACT

A needleless connector has a body having an internal cavity with a sealing ridge, a port, an output flow channel, and a fluid flow path between the port and output flow channel. The connector also has a collapsible valve disposed within the cavity. The valve includes a cylindrical wall having a center axis, an internal surface, and a shoulder configured to sealingly contact the ridge of the body, thereby blocking the fluid flow path. The valve also includes a head fixedly attached to the wall. The head has a smiley cut at a first angular position about the center axis and a continuous top surface that is generally perpendicular to the axis. The valve also includes a first dimple formed in the internal surface of the cylindrical wall. The dimple extends around the internal surface over an angle in the range of 90-270°.

16 Claims, 4 Drawing Sheets section B-B

(51) Int. Cl.
*A61M 39/26* (2006.01)
*A61M 39/10* (2006.01)

(56) References Cited

U.S. PATENT DOCUMENTS

| | | |
|---|---|---|
| 4,654,031 A | 3/1987 | Lentz |
| 4,911,403 A | 3/1990 | Lockwood, Jr. |
| 5,092,857 A | 3/1992 | Fleischhacker |
| 5,549,651 A | 8/1996 | Lynn |
| 5,555,908 A * | 9/1996 | Edwards ............... A61M 39/26 137/329.1 |
| 5,623,969 A | 4/1997 | Raines |
| 5,690,612 A | 11/1997 | Lopez et al. |
| 5,699,821 A | 12/1997 | Paradis |
| 5,730,418 A | 3/1998 | Feith et al. |
| 5,782,816 A | 7/1998 | Werschmidt et al. |
| 5,992,462 A | 11/1999 | Atkinson et al. |
| 6,024,729 A | 2/2000 | Dehdashtian et al. |
| 6,050,978 A | 4/2000 | Orr et al. |
| 6,245,048 B1 | 6/2001 | Fangrow, Jr. et al. |
| 6,679,219 B1 | 1/2004 | Pacinelli |
| 6,886,803 B2 | 5/2005 | Mikiya et al. |
| 7,184,825 B2 | 2/2007 | Leinsing et al. |
| 8,291,936 B2 | 10/2012 | Carmody et al. |
| 8,568,371 B2 | 10/2013 | Siopes et al. |
| 2002/0193752 A1 | 12/2002 | Lynn |
| 2003/0050610 A1 | 3/2003 | Newton et al. |
| 2003/0098430 A1 | 5/2003 | Leinsing et al. |
| 2005/0059952 A1 | 3/2005 | Giuliano et al. |
| 2005/0222541 A1 | 10/2005 | Lopez et al. |
| 2006/0025724 A1 | 2/2006 | Chen |
| 2006/0027270 A1 | 2/2006 | Truitt et al. |
| 2006/0089603 A1 | 4/2006 | Truitt et al. |
| 2006/0163515 A1 | 7/2006 | Ruschke |
| 2006/0208210 A1 * | 9/2006 | Raybuck ............... A61M 39/26 251/149.1 |
| 2007/0270756 A1 | 11/2007 | Peppel et al. |
| 2008/0108956 A1 | 5/2008 | Lynn et al. |
| 2009/0030401 A1 | 1/2009 | Phillips |
| 2009/0057589 A1 | 3/2009 | Thorne, Jr. et al. |
| 2009/0299300 A1 * | 12/2009 | Truitt ............... A61M 39/02 604/246 |
| 2010/0036330 A1 | 2/2010 | Plishka et al. |
| 2010/0256573 A1 | 10/2010 | Mansour et al. |
| 2011/0028914 A1 | 2/2011 | Mansour et al. |
| 2011/0028915 A1 | 2/2011 | Siopes et al. |
| 2011/0046573 A1 | 2/2011 | Newton et al. |
| 2011/0130724 A1 | 6/2011 | Mansour et al. |
| 2011/0152787 A1 | 6/2011 | Truitt et al. |
| 2012/0310179 A1 | 12/2012 | Truitt et al. |
| 2012/0316514 A1 | 12/2012 | Mansour |
| 2013/0030386 A1 | 1/2013 | Panian et al. |
| 2013/0190684 A1 | 7/2013 | Panian et al. |

FOREIGN PATENT DOCUMENTS

| | | |
|---|---|---|
| CN | 1305391 A | 7/2001 |
| CN | 102481445 A | 5/2012 |
| CN | 102497897 A | 6/2012 |
| CN | 102686265 A | 9/2012 |
| EP | 2075032 A1 | 7/2009 |
| EP | 2719419 A1 | 4/2014 |
| WO | WO-9826835 A1 | 6/1998 |
| WO | WO-2004082756 A1 | 9/2004 |
| WO | WO-2004/112866 A2 | 12/2004 |
| WO | WO-2005011799 A1 | 2/2005 |
| WO | WO 2005011799 A1 * | 2/2005 ........ A61M 39/045 |
| WO | WO-2006078355 A1 | 7/2006 |
| WO | WO-2008091698 A2 | 7/2008 |
| WO | WO-2011014265 A1 | 2/2011 |
| WO | WO-2011060384 A1 | 5/2011 |
| WO | WO-2013016077 A2 | 1/2013 |
| WO | WO-2013099261 A1 | 7/2013 |
| WO | WO-2013122148 A1 | 8/2013 |

OTHER PUBLICATIONS

International Search Report and Written Opinion for the International Preliminary Examining Authority for Application No. PCT/US2014/017824, dated Mar. 23, 2015, 6 pages.
Extended European Search Report for Application No. 14158885.5, dated May 12, 2014.
International Search Report and Written Opinion for Application No. PCT/US2014/017480, dated May 13, 2014.
International Search Report and Written Opinion for Application No. PCT/US2014/017826, dated May 8, 2014.
International Search Report and Written Opinion for Application No. PCT/US2014/017828, dated May 2, 2014.
Extended European Search Report for Application No. 1415882.2, dated Jul. 7, 2014.
International Search Report and Written Opinion for Application No. PCT/US2014/017824, dated May 9, 2014.
Extended European Search Report for European Application No. 14158882.2, dated Jul. 7, 2014, 7 pages.
Extended European Search Report in Application No. 14158891.3, dated Jul. 8, 2014, 6 pages.
Extended European Search Report for Application No. 14158899.6, dated Jul. 8, 2014, 6 pages.
International Search Report and Written Opinion for Application No. PCT/US2014/017486, dated May 13, 2014, 14 pages.
International Search Report and Written Opinion for Application No. PCT/US2014/023694, dated Jun. 26, 2014, 11 pages.
Chinese Office Action for Application No. 2014800143520, dated Dec. 5, 2016, 7 pages.
European Office Action for Application No. 14/708451.1, dated Nov. 30, 2016, 3 pages.
Partial Supplementary European Search Report for Application No. 14778965.5, dated Dec. 16, 2016, 7 pages excluding translation.
Chinese Office Action for Application No. 201480014557.9, dated Mar. 3, 2017, 6 pages excluding English translation.
Chinese Office Action for Application No. 201480014971.X, dated Feb. 21, 2017, 6 pages excluding English translation.
Chinese Office Action for Application No. 201480015065.1, dated Feb. 22, 2017, 7 pages excluding English translation.
Chinese Office Action for Application No. 201480014965.4, dated Mar. 3, 2017, 9 pages excluding English translation.
Chinese Office Action for Application No. 201480015027.6, dated Mar. 10, 2017, 7 pages.

* cited by examiner

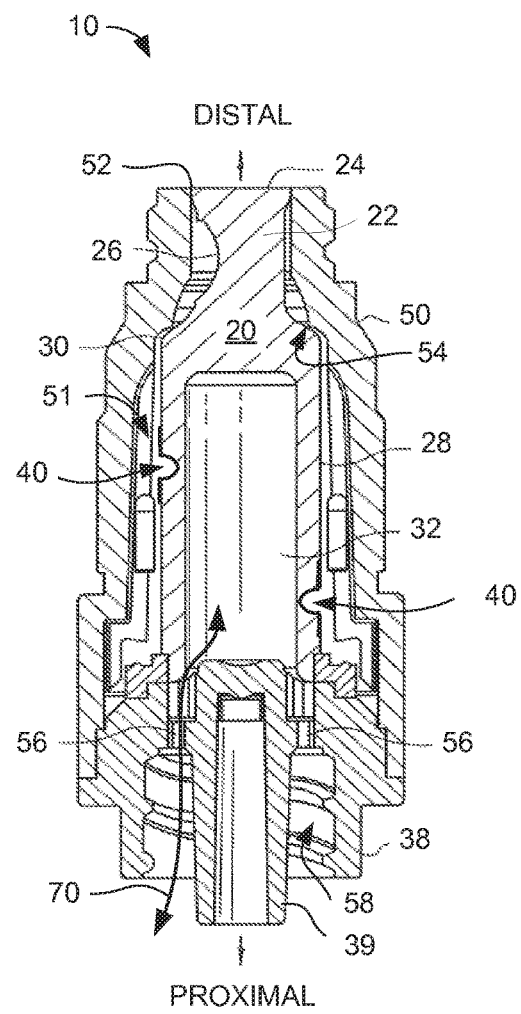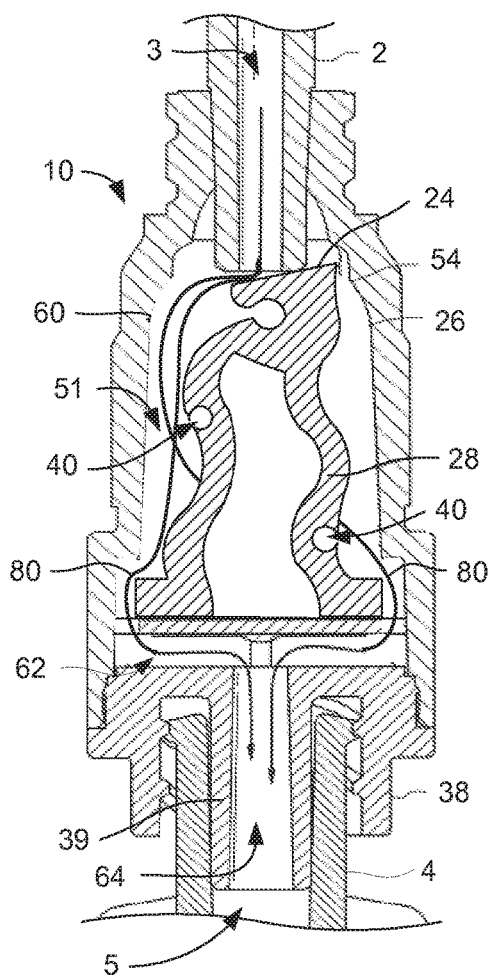
FIG. 1A
PRIOR ART
FIG. 1B
PRIOR ART section B-B section C-C section D-D section E-E

COLLAPSIBLE VALVE WITH INTERNAL DIMPLES

CROSS-REFERENCES TO RELATED APPLICATIONS

This application is a continuation of application Ser. No. 13/801,399, filed on Mar. 13, 2013, entitled, "COLLAPSIBLE VALVE WITH INTERNAL DIMPLES," the disclosures of which are hereby incorporated by reference in its entirety.

BACKGROUND

Field

The present disclosure generally relates to needleless connectors, and, in particular, to connectors with an internal collapsible valve.

Description of the Related Art

Medical treatments often include the infusion of a medical fluid, for example a saline solution or a liquid medication, to patients using an intravenous (IV) catheter that is connected though an arrangement of flexible tubing and fittings, commonly referred to as an "IV set," to a source of fluid, for example an IV bag. The fittings commonly include interconnectable male and female needleless connectors having a "Luer taper" conforming to an International Standards Organization (ISO) standard. Certain connectors have a self-sealing feature to prevent leakage of fluid from the attached tubing when the connector is decoupled from a mating connector.

One challenge with certain conventional needleless self-sealing connectors is that the medical fluid passing through the connector may become trapped in crevices and recesses within the connector. As certain types of medical fluids may degrade within a treatment time period, retention of medical fluid within the connector is undesirable.

SUMMARY

It is advantageous to provide a needleless connector that does not trap fluid within the connector during use. The disclosed female connector provides a smooth surface within the fluid path through the connector by positioning dimples that guide the collapse of the internal valve on a surface that is not wetted by the fluid.

In certain embodiments, a needleless connector is disclosed that includes a body having an internal cavity with a sealing ridge, a port, an output flow channel, and a fluid flow path between the port and output flow channel. The connector also includes a collapsible valve disposed within the cavity. The valve comprises a cylindrical wall having a center axis, an internal surface, and a shoulder configured to sealingly contact the ridge of the body, thereby blocking the fluid flow path. The valve also comprises ahead fixedly attached to the wall. The head has a smiley cut at a first angular position about the center axis and a continuous top surface that is generally perpendicular to the axis. The valve also comprises a first dimple formed in the internal surface of the cylindrical wall, the dimple extending around the internal surface over an angle in the range of 90-270°.

In certain embodiments, a collapsible valve is disclosed that includes a cylindrical wall having a center axis and an internal surface and a head fixedly attached to the wall. The head has a smiley cut at a first angular position about the center axis and a continuous top surface that is generally perpendicular to the axis. The valve also includes a first dimple formed in the internal surface of the cylindrical wall. The dimple extends around the internal surface over an angle in the range of 90-270°.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 1A-1B are cross-sections of a conventional connector illustrating how fluid may become trapped within the connector body.

DETAILED DESCRIPTION

Figure 2A:
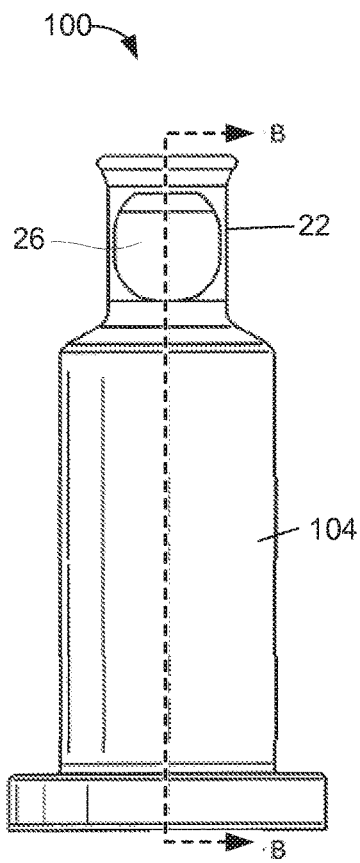
FIGS. 2A-2C depict an exemplary collapsible valve according to certain aspects of the present disclosure.

It is advantageous to provide a needleless connector that does not trap fluid within the connector during use. The disclosed female connector provides a smooth surface within the fluid path through the connector by positioning dimples that guide the collapse of the internal valve on a surface that is not wetted by the fluid.

In the following detailed description, numerous specific details are set forth to provide a full understanding of the present disclosure. It will be apparent, however, to one ordinarily skilled in the art that embodiments of the present disclosure may be practiced without some of the specific details. In other instances, well-known structures and techniques have not been shown in detail so as not to obscure the disclosure. In the referenced drawings, like numbered elements are the same or essentially similar. Reference numbers may have letter suffixes appended to indicate separate instances of a common element while being referred to generically by the same number without a suffix letter.

While the following discussion is directed to the administration of medical fluid to a patient by a nurse using an IV set having the disclosed connectors, this is only an example of usage and does not limit the scope of the claims. The disclosed connectors may be used in any application where it is desirable to avoid trapping fluid within a self-sealing connector.

FIGS. 1A-1B are cross-sections of a conventional connector 10 illustrating how fluid may become trapped within the connector body 50. With reference to FIG. 1A, the connector 10 includes a collapsible valve 20 disposed within a cavity 51 of body 50. The valve 20 has a shoulder 30 that continuously contacts a ridge 54 within the cavity 51 when the connector 10 is de-activated, i.e. not connected to a mating connector, to form a primary seal that blocks the fluid flow path through the connector 10. At the same time, a top surface 24 of the valve 20 is positioned generally flush with a port 52 of the cavity 51 and the edge of the continuous top surface 24 seals to the port 52. The top surface 24 is continuous, i.e. there is no slit or penetration in the surface that may trap bacteria or other contamination. The valve 20 has an internal air space 32 that is separated from the cavity 51 by a cylindrical wall 28. The air space 32 is vented to the ambient environment through air passages 56 and the external cavity 58 within the threaded connector 38 surrounding the male Luer fitting 39 of the body 50, as indicated by the air flow path 70. The valve 20 also has a solid head 22 with a "smiley cut" 26 formed on one side.

The valve 20 has a pair of external dimples 40 formed in the wall 28 that control the collapse of the valve 20 when an axial force is applied to the external surface 24. The two dimples 40 are typically on opposite sides of the wall 28 and axially offset from each other. The center of the dimples 40 are aligned in a common place with the center of the smiley cut 26.

FIG. 1B depicts the valve 10 in the activated position, i.e. a male Luer fitting 2 sealingly coupled to the connector 10 at port 52. The tip of the male Luer fitting 2 has displaced the external surface 24 downward and the applied force has caused the head 22 to buckle toward the smiley cut 26 as well as causing the cylindrical wall 28 to buckle in a plane that passes through the two external dimples 40. The primary seal between the shoulder 30 and ridge 54 is opened such that the fluid flow path through the connector 10 is open, as indicated by the fluid flow path 80 that passes from the lumen 3 of the male Luer fitting 2 through the cavity 51 and through channels 62 in the base and out through an output flow channel 64 of the male fitting 39 that is fluidly coupled to the flow channel 5 of the connected female Luer fitting 4. Air passes out of the air chamber 32 along the air flow path 70 as the valve 20 collapses.

It can be seen in FIG. 1B that the external dimples 40 have folded over and formed enclosed spaces that may trap a portion of the fluid passing through the cavity 51. Even if the enclosed spaces are not completely sealed, there may be very little if any circulation through the enclosed spaces and, therefore, fluid remains static within the enclosed spaces. As certain types of medical fluids may degrade within the time period that it takes to administer the medical fluid, retention of the medical fluid within the connector may allow the medical fluid to degrade before reaching the patient.

Figure 2B:
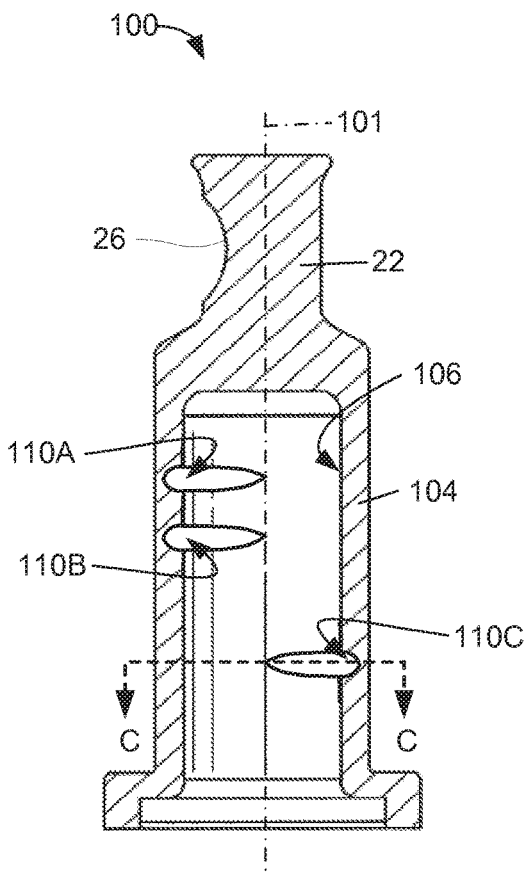
Figure 2C:
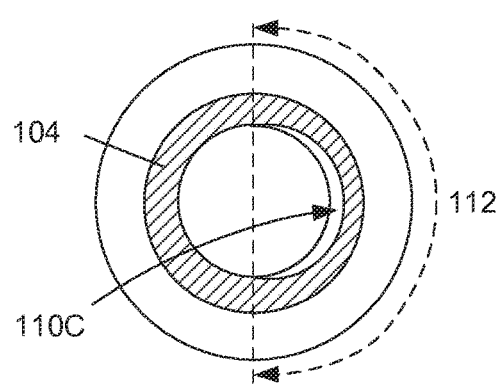

FIGS. 2A-2C depict an exemplary collapsible valve 100 according to certain aspects of the present disclosure. FIG. 2A is an external view showing the head 22 with a smiley cut 26 and a cylindrical wall 104.

FIG. 2B is a cross-section of the valve 100 taken along the section line B-B shown in FIG. 2A. In this embodiment, there are three internal dimples 110, labeled as 110A, 110B, and 110C, formed in an internal surface 106 of the wall 104. In this example, dimples 110A and 110B are in close axial proximity to each other and angularly aligned with each other about a center axis 101. The dimple 110C is, in this example, axially offset from both of the dimples 110A, 110B and positioned 180° away from the dimples 110A, 110B about the axis 101. In certain embodiments, there may be only a single internal dimple 110. In certain embodiments, there may be two dimples 110. In certain embodiments, the two dimples 110 may be axially aligned with each other, i.e. with their centers on a common plane (not shown) that is perpendicular to the axis 101. In certain embodiments, the dimples 110 have a common depth that is approximately half the thickness of the wall 104. In certain embodiments, the dimples 110 may have different depths. In certain embodiments, one dimple 110 may be angularly offset about the axis 101 from another dimple 110.

FIG. 2C is a cross-section taken of a complete valve 100 at the location indicated by the section line C-C in FIG. 2B. It can be seen that the dimple 110C, in this example, has a variable depth over the circumferential length of the dimple 110C that extends over an angle 112. In this example, the depth is zero at the tips with a maximum at the center of the dimple 110C. In certain embodiments, the depth may be constant over the angle 112. In FIG. 2C, the angle is approximately 180°. In certain embodiments, the angle may be greater than or less than 180°.

Figure 3:
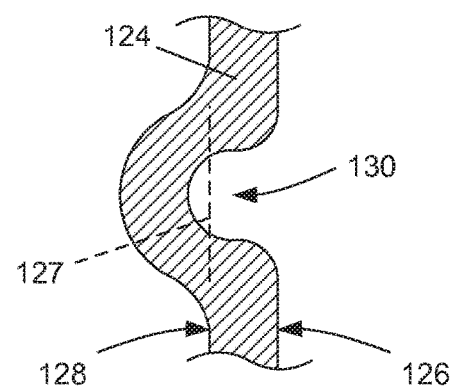
FIG. 3 is a cross-section of an example embodiment of an internal dimple according to certain aspects of the present disclosure.

FIG. 3 is a cross-section of an example embodiment of an internal dimple 130 formed in an inner surface 126 of a wall 124 wherein the external surface 128 of the wall 124 is deformed adjacent to the dimple 110 such that the dimple 130 has a depth that is greater than the thickness of the wall 124.

Figure 4A:
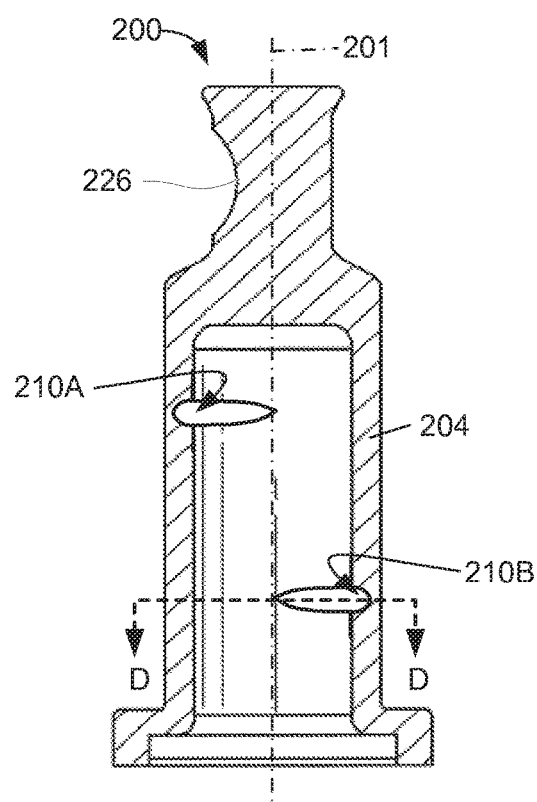
FIGS. 4A-4B depict another embodiment of a collapsible valve according to certain aspects of the present disclosure.
Figure 4B:
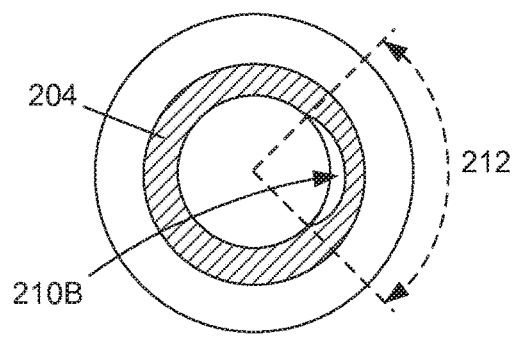

FIGS. 4A-4B depict another embodiment of a collapsible valve 200 according to certain aspects of the present disclosure. FIG. 4A is a cross-section of the entire valve 200 showing that the collapsible valve 200 has two internal dimples 210A, 210B formed in wall 204 that are axially offset from each other and aligned with the smiley cut 26 on opposite sides of the center axis 201.

FIG. 4B is a cross-section taken of a complete valve 200 at the location indicated by the section line D-D in FIG. 4A. The dimple 210B has an angular span of angle 212 that is, in this example, approximately 90°.

Figure 5A:
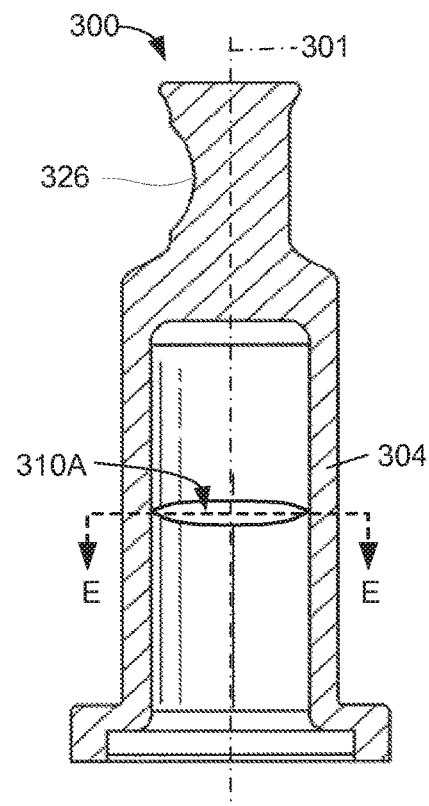
FIGS. 5A-5B depict another embodiment of a collapsible valve to certain aspects of the present disclosure.
Figure 5B:
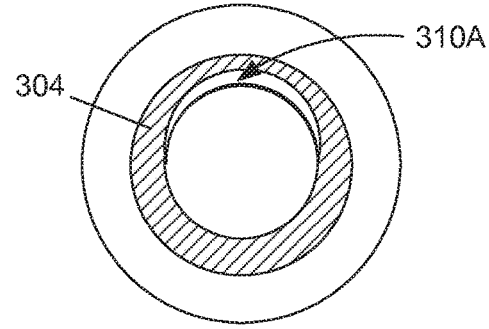

FIGS. 5A-5B depict another embodiment of a collapsible valve 300 according to certain aspects of the present disclosure. FIG. 5A is a cross-section of the entire valve 300 showing that the collapsible valve 300 has internal dimple 310A with a second dimple 310B (not visible in FIG. 5A) formed on the opposite side of the wall 304. The dimples 310A, 310B are aligned with each other in a common plane that passes through the center axis 301 and is perpendicular to the location of the smiley cut 326 relative to the axis 301.

FIG. 5B is a cross-section taken of a complete valve 300 at the location indicated by the section line E-E in FIG. 5A. The dimple 310A has an angular span of angle 212 that is, in this example, approximately 100° and is formed at a location that is approximately 90° offset about the axis 301 from the angular position of the smiley cut 326.

Figure 6:
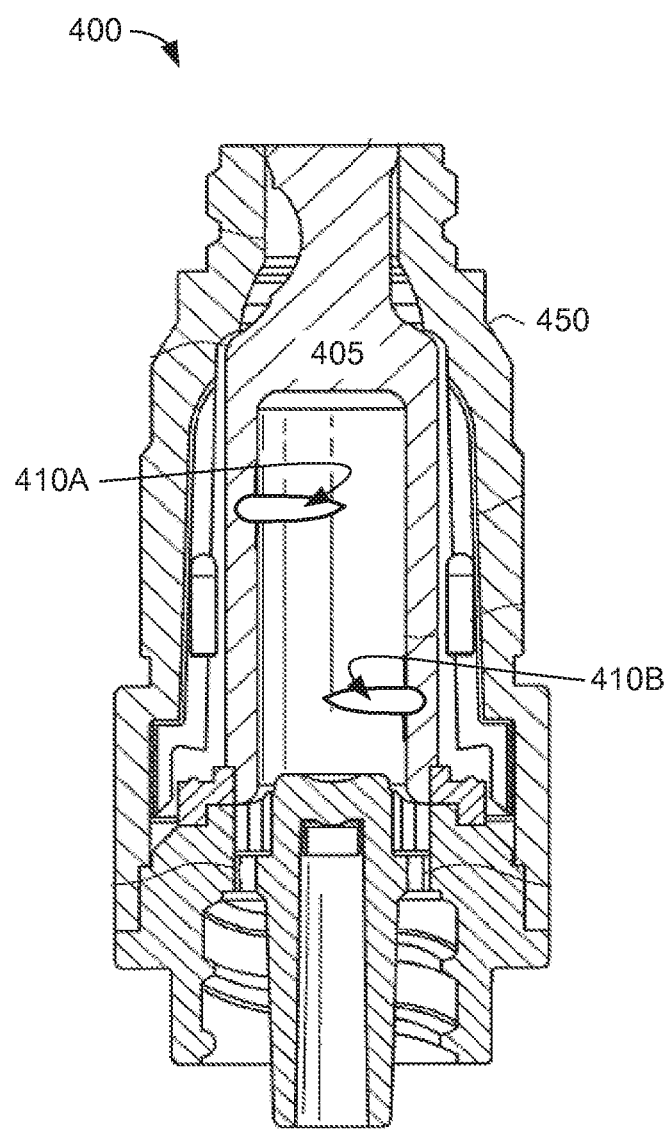
FIG. 6 is a cross-section of an exemplary needleless connector having a collapsible valve with internal dimples according to certain aspects of the present disclosure.

FIG. 6 is a cross-section of an exemplary needleless connector 400 having a collapsible valve 405 with internal dimples 410 according to certain aspects of the present disclosure. The body 450 is generally similar to the body 50 of the connector 10 of FIGS. 1A-1B. The valve 405 has two internal dimples 410A, 410B that are axially offset and arranged on opposite sides of the valve 405, similar to the valve 200 of FIGS. 4A-4B. Other features of the valve 405 are generally similar to the valve 20 of connector 10.

It can be seen that the disclosed embodiments of the needleless connector provide a fluid flow path that does not trap fluid within folded dimples on the external surface of a collapsible internal valve. Positioning the dimples within the internal air space separates the dimples from the fluid path while still providing control of the collapse of the disclosed valve.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to he inclusive in a manner similar to the term "comprise" as "comprise" is interpreted when employed as a transitional word in a claim.

What is claimed is:

1. A needleless connector comprising:
   a body having an internal cavity; and
   a collapsible valve disposed within the internal cavity, the valve, when unrestrained, comprising:
   a cylindrical wall having a center axis, an internal surface, an external surface, and a first concave cut-out on the internal surface extending away the center axis, wherein the first concave cut-out extends around the internal surface over an angle in the range of only 90-270 degrees, and a protruding portion of the external surface of the cylindrical wall aligned with the first concave cut-out protrudes radially away from the center axis, and wherein the external surface adjacent the protruding portion does not extend toward the center axis; and
   a head fixedly attached to the cylindrical wall, the head having a second concave cut-out extending toward the center axis.

2. The needleless connector of claim 1, wherein the body comprises a first port, a second port opposite the first port, a flow channel between the first and second port; and the external surface of the cylindrical wall comprises a shoulder configured to sealingly contact an internal surface of the body, thereby blocking the flow channel.

3. The needleless connector of claim 1, wherein the head comprises a continuous top surface that is generally perpendicular to the axis.

4. The needleless connector of claim 1, wherein the first concave cut-out extends around the internal surface of the cylindrical wall in a plane that is perpendicular to the center axis.

5. The needleless connector of claim 1, further comprising a third concave cut-out formed on the internal surface of the cylindrical wall and extending around the internal surface over an angle in the range of 90-270 degrees, the third concave cut-out being axially offset from the first concave cut-out.

6. The needleless connector of claim 5, wherein the third concave cut-out is angularly offset about the center axis from the first concave cut-out by an angle of approximately 180 degrees.

7. The needleless connector of claim 5, wherein the first concave cut-out or the third concave cut-out is angularly offset about the center axis from the second concave cut-out angle in the range of 90-270 degrees.

8. The needleless connector of claim 1, wherein the first concave cut-out is angularly offset about the center axis from the second concave cut-out by an angle of approximately 180 degrees.

9. The needleless connector of claim 1, wherein (i) the collapsible valve comprises an internal air space formed within the cylindrical wall, the air space having a bottom opening; and (ii) the body comprises air passages that provide an air flow path between the air space of the collapsible valve and the ambient environment.

10. A collapsible valve comprising:
    a cylindrical wall having a center axis, an internal surface, an external surface, and a first concave cut-out on the internal surface extending away the center axis, wherein a protruding portion of the external surface of the cylindrical wall aligned with the first concave cut-out protruding radially away from the center axis when the valve is unrestrained; and
    a head fixedly attached to the cylindrical wall, the head having a second concave cutout extending toward the center axis, wherein the second concave cut-out is angularly offset about the center axis relative to the first concave cut-out;
    wherein the first concave cut-out extends around the internal surface of the cylindrical wall over an angle in the range of 90-270 degrees.

11. The needleless connector of claim 10, wherein the head comprises a continuous top surface that is generally perpendicular to the axis.

12. The needleless connector of claim 10, wherein the first concave cut-out extends around the internal surface of the cylindrical wall in a plane that is perpendicular to the center axis.

13. The needleless connector of claim 10, further comprising a third concave cut-out formed on the internal surface of the cylindrical wall and extending around the internal surface over an angle in the range of 90-270 degrees, the third concave cut-out being axially offset from the first concave cut-out.

14. The needleless connector of claim 13, wherein the third concave cut-out is angularly offset about the center axis from the first concave cut-out by an angle of approximately 180 degrees.

15. The needleless connector of claim 13, wherein the first concave cut-out or the third concave cut-out is angularly offset about the center axis from the second concave cut-out angle in the range of 90-270 degrees.

16. The needleless connector of claim 10, wherein the first and second concave cut-outs are angularly offset by an angle of approximately 180 degrees.

* * * * *